United States Patent [19]
Foo

[11] Patent Number: 5,251,628
[45] Date of Patent: Oct. 12, 1993

[54] VARIABLE ECG DELAY IN FAST PULSE SEQUENCE SCANS

[75] Inventor: Thomas K. Foo, Waukesha, Wis.

[73] Assignee: General Electric Company, Milwaukee, Wis.

[21] Appl. No.: 902,627

[22] Filed: Jun. 23, 1992

[51] Int. Cl.[5] .............................................. A61B 5/055
[52] U.S. Cl. .................................. 128/653.2; 128/708
[58] Field of Search ............................ 128/653.2, 708; 324/309

[56] References Cited

U.S. PATENT DOCUMENTS

| | | | |
|---|---|---|---|
| 4,710,717 | 12/1987 | Pelc et al. | 128/653.2 |
| 4,968,935 | 11/1990 | Ehman et al. | 324/309 |
| 4,986,272 | 1/1991 | Riederer et al. | 128/653 |

OTHER PUBLICATIONS

The Importance of Phase-Encoding Order in Ultra-Short TR Snapshot MR Imaging, Holsinger, et al., Magnetic Resonance in Medicine, 16, 418–488 (1990).
Comparing the FAISE Method with Conventional Dual-Echo Sequences[1], Melki et al., JMRI pp. 319–326, May/Jun. 1991.

*Primary Examiner*—Ruth S. Smith
*Attorney, Agent, or Firm*—Quarles & Brady

[57] ABSTRACT

An NMR system performs a pulmonary vascular scan comprised of a series of slice acquisition. Each slice acquisition employs a series of fast pulse sequences (GRASS) which are completed in one cardiac cycle. The view order of each slice acquisition is altered such that the low order views are acquired at a desired contrast delay interval after receipt of a cardiac trigger signal.

6 Claims, 4 Drawing Sheets

VARIABLE ECG DELAY IN FAST PULSE SEQUENCE SCANS

BACKGROUND OF THE INVENTION

The field of the invention is nuclear magnetic resonance imaging methods and systems. More particularly, the invention relates to ECG triggered vascular imaging using fast NMR pulse sequences for both the pulmonary vasculature and the peripheral vasculature where pulsatile blood flow is prevalent.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant $\gamma$ of the nucleus). Nuclei which exhibit this phenomena are referred to herein as "spins".

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$, which is rotating, or spinning, in the x-y plane at the Larmor frequency. The practical value of this phenomenon resides in the signal which is emitted by the excited spins after the excitation signal $B_1$ is terminated. There are a wide variety of measurement sequences in which this nuclear magnetic resonance ("NMR") phenomena is exploited.

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well known reconstruction techniques. To perform such a scan, it is, of course, necessary to elicit NMR signals from specific locations in the subject. This is accomplished by employing magnetic fields ($G_x$, $G_y$, and $G_z$) which have the same direction as the polarizing field $B_0$, but which have a gradient along the respective x, y and z axes. By controlling the strength of these gradients during each NMR cycle, the spatial distribution of spin excitation can be controlled and the location of the resulting NMR signals can be identified.

Most NMR scans currently used to produce medical images require many minutes to acquire the necessary data. The reduction of this scan time is an important consideration, since reduced scan time increases patient throughput, improves patient comfort, and improves image quality by reducing motion artifacts. There is a class of pulse sequences which have a very short repetition time (TR) and result in complete scans which can be conducted in seconds rather than minutes. Whereas the more conventional pulse sequences have repetition times TR which are much greater than the spin-spin relaxation constant $T_2$ so that the transverse magnetization has time to relax between the phase coherent excitation pulses in successive sequences, the fast pulse sequences have a repetition time TR which is less than $T_2$ and which drives the transverse magnetization into a steady-state of equilibrium. Such techniques are referred to as steady-state free precession (SSFP) techniques and they are characterized by a cyclic pattern of transverse magnetization in which the resulting NMR signal refocuses at each RF excitation pulse to produce an echo signal. This echo signal includes a first part S+ that is produced after each RF excitation pulse and a second part S− which forms just prior to the RF excitation pulse.

There are two well known SSFP pulse sequences used to produce images. The first is called gradient refocused acquired steady-state (GRASS) and it utilizes a readout gradient $G_x$ to shift the peak in the S+ signal that is produced after each RF excitation pulse toward the center of the pulse sequence. In two-dimensional imaging, a slice selection gradient pulse is produced by the gradient $G_z$ and is immediately refocused in the well-known manner. A phase encoding gradient pulse $G_y$ is produced shortly thereafter to position encode the acquired NMR data, and to preserve the steady-state equilibrium, the effects of the phase encoding gradient pulse are nullified by a corresponding $G_y$ rewinder gradient pulse after the NMR signal has been acquired and before the next pulse sequence begins as described in U.S. Pat. No. 4,665,365.

The second well known SSFP pulse sequence is called contrast enhanced fast imaging (SSFP-ECHO) and it utilizes the S− signal that is produced just prior to each RF excitation pulse. In this pulse sequence the acquired NMR signal is an S− echo signal caused by the gradient refocusing of the transverse magnetization which would otherwise refocus at the next RF excitation pulse. The readout gradient $G_x$ is substantially different in this pulse sequence and includes a positive pulse prior to the actual readout pulse and a negative pulse after the readout pulse. The former pulse dephases the FID signal (S+) which might otherwise be produced during the data acquisition window, and the latter pulse causes the transverse magnetization to rephase during the next pulse sequence to produce the echo signal S−. For a more detailed discussion of the SSFP-ECHO pulse sequence, reference is made to an article by R. C. Hawkes and S. Patz entitled "Rapid Fourier Imaging Using Steady-State Free Precision", published in *Magnetic Resonance in Medicine* 4, pp. 9–23 (1987).

The fast NMR pulse sequences can be used to great advantage when imaging the vasculature of the lungs. Since a complete slice using such a pulse sequence can be acquired in approximately one second, it is possible in a single breath hold by the subject to acquire a series of 2D slices. This is in contrast to conventional techniques which require minutes for each slice and must employ respiratory gating to reduce blurring caused by respiratory movements.

To enhance the contrast between pulmonary vessels and surrounding tissues, the acquisition of the NMR data is synchronized with the subject's cardiac cycle. For example, maximum signal intensity in the pulmonary arteries is attained in the late systole or early diastole portions of the cardiac cycle. Since image contrast is determined primarily by the central, or low spatial views of the scan, this suggests that the start of each scan be delayed for a specific time interval after the detection of the cardiac trigger such that the central views are acquired at the proper moment.

Such delays of 50 to 600 milliseconds have little impact on the scan time using conventional pulse sequence, but the impact on fast pulse sequence pulmonary vascular imaging can be substantial. This is illustrated in FIG. 1, which depicts an ECG signal 10 produced at a heart rate of 60 beats/minute. The R-R interval of the ECG signal 10 is approximately one second, and using fast sequences a complete slice acquisition 11 with 128 views can be acquired during each R-R interval if it is commenced at the beginning of the cardiac cycle when the ECG trigger signal is generated. Consequently, a typical scan of 12 to 16 slices can be acquired within 16 seconds, which can be accomplished within a single breath hold of even an infirm patient. However, if the slice acquisition is delayed for 400 milliseconds in order to attain higher signal intensity in the arteries, the slice acquisition overlaps into the next cardiac cycle as shown at 12. As a result, two one second cardiac cycles are required for each slice acquisition 12 and the total scan time is doubled. The resulting 24 to 32 second scan is very difficult for some patients to complete in a single breath hold, and the primary advantage of using the fast pulse sequence in this application is lost.

Although the method of a variable ECG delay by view reordering is particularly applicable in imaging the pulmonary vessels, the method can also be applied to vascular imaging in any region where pulsatile flow is a problem. Pulsatile flow generates artifacts in conventional acquisition pulse sequences which degrades image quality and prevents accurate diagnosis. Since the sequence repetition times (TR) for a conventional vascular imaging sequence is of the order of 30–50 ms, conventional cardiac gating where a single line of k-space is acquired per cardiac trigger results in image acquisition times of the order of 2 min per image. In order to generate a time-of-flight vascular imaging, several sections are required. This poses a problem in peripheral vascular imaging where a 30–60 cm region must be covered. Conventional ECG gating is impractical as the scan time is about 60 min for a complete series of images. Variable ECG delay by view reordering permits an image to be acquired in 1-2 seconds. Thus, a series of 30-60 images necessary to generate a time-of-flight vascular image requires a scan time of 1-2 minutes. This represents a significant time savings in addition to improving the image quality.

SUMMARY OF THE INVENTION

The present invention relates to the acquisition of an NMR data set comprised of a plurality of slice acquisitions in which each slice is acquired with a series of fast pulse sequences commenced in synchronism with the subject's cardiac cycle. More specifically, the sequence in which a phase encoding magnetic field gradient in each fast pulse sequence is stepped through its discrete values during the slice acquisition is reordered such that the central views of the slice are acquired at a preselected time interval after the generation of a cardiac trigger signal to provide a desired image contrast.

A general object of the invention is to provide an effective delay in the acquisition of each slice with respect to a cardiac trigger signal without increasing the total scan time. Since image contrast is determined primarily by the central views, the desired contrast can be obtained by delaying the acquisition of the central views by the required amount. Peripheral views, on the other hand, may be obtained beforehand such that the data acquisition can begin immediately after the cardiac trigger signal and the entire series of slice pulse sequences can be completed during a single cardiac cycle. The order in which the views are acquired can be changed from slice-to-slice such that the central views are always acquired with the requisite contrast delay.

Another object of the invention is to reorder the sequence of views in a fast pulse sequence scan to provide a desired delay contrast without introducing image artifacts. A centric-view ordering is employed to reduce artifacts caused by the rapid switching of the phase encoding magnetic field gradient. This centric-view order is rotated by an amount which enables the central views to be acquired at the desired delay interval.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DETAILED DESCRIPTION OF THE INVENTION

Figure 2:
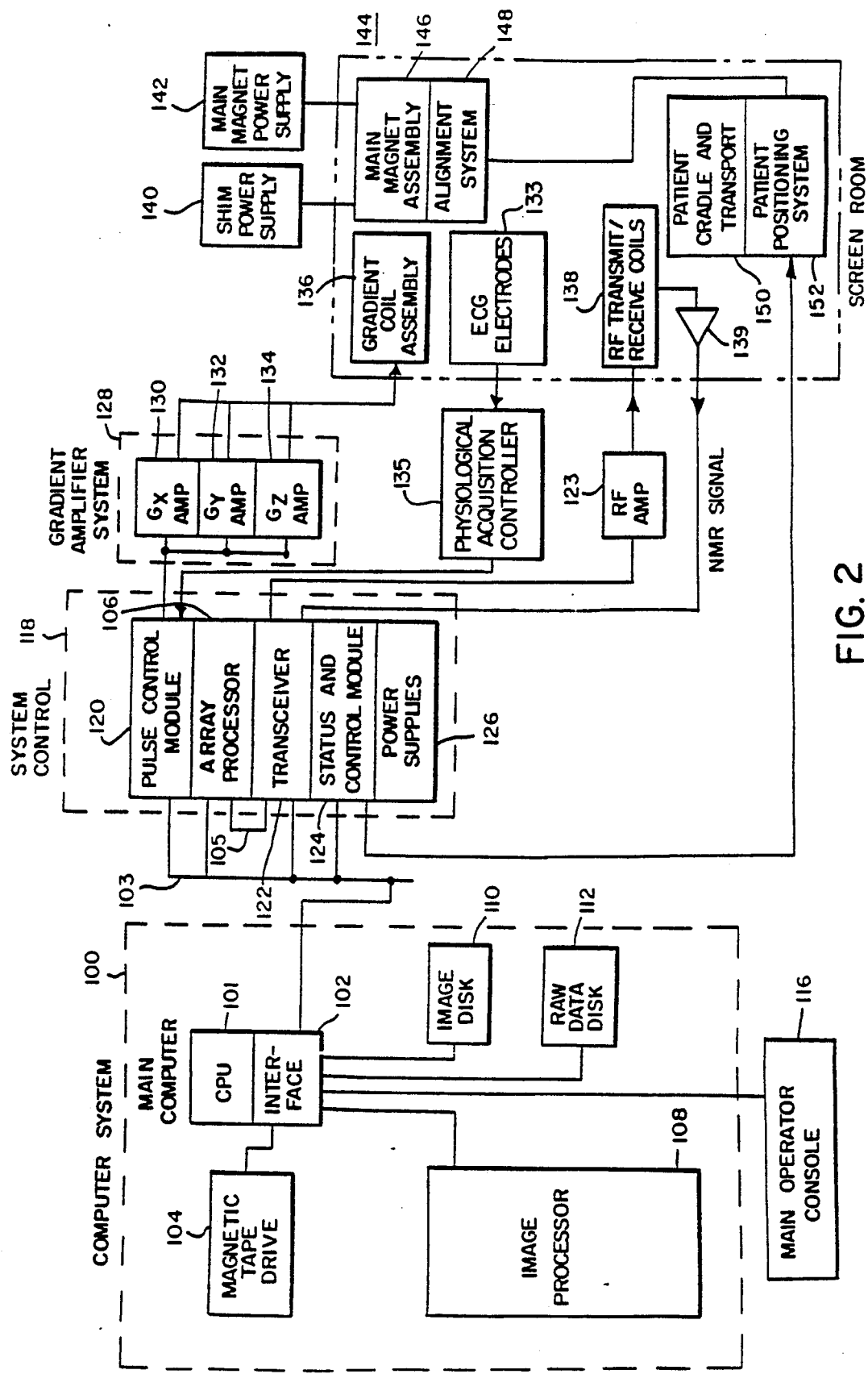
FIG. 2 is a block diagram of an NMR system which employs the present invention.

Referring first to FIG. 2, there is shown in block diagram form the major components of a preferred NMR system which incorporates the present invention and which is sold by the General Electric Company under the trademark "SIGNA". The overall operation of the system is under the control of a host computer system generally designated 100 which includes a main computer 101 (such as a Data General MV7800). The computer has associated therewith an interface 102 through which a plurality of computer peripheral devices and other NMR system components are coupled. Among the computer peripheral devices is a magnetic tape drive 104 which may be utilized under the direction of the main computer for archiving patient data and images to tape. Processed patient data may also be stored in an image disc storage device designated 110. The function of image processor 108 is to provide interactive image display manipulation such as magnification, image comparison, gray-scale adjustment and real-time data display. The computer system is provided with a means to store raw data (i.e. before image construction) utilizing a disc data storage system designated 112. An operator console 116 is also coupled to the computer by means of interface 102 and provides the operator with the means to input data pertinent to a patient study as well as additional data necessary for proper NMR system operation, such as calibrating, initiating and terminating scans. The operator console is also used to display images stored on discs or magnetic tape.

The computer system 100 exercises control over the NMR system by means of system control 118 and gradient amplifier system 128. The computer 100 communicates with system control 118 by means of a link 103 in a manner well known to those skilled in the art. The system control 118 includes several subsystems such as a pulse control module (PCM) 120, an array processor 106, a radio frequency transceiver 122, a status and control module (SCM) 124, and the power supplies generally designated 126 necessary to energize the components. The PCM 120 utilizes control signals provided by main computer 101 to generate digital timing and control signals such as the digital waveforms which control gradient coil excitation, as well as RF envelope waveforms utilized in the transceiver 122 for modulating the RF excitation pulses. The gradient waveforms are applied to the gradient amplifier system 128 generally comprised of $G_x$, $G_y$ and $G_z$ amplifiers 130, 132 and 134, respectively. Each amplifier 130, 132 and 134 is utilized to excite a corresponding gradient coil in an assembly generally designated 136. When energized, the gradient coils generate magnetic field gradients $G_x$, $G_y$ and $G_z$ of the magnetic field in the same direction as the main polarizing magnetic field, wherein the gradients are directed in mutually orthogonal X-, Y- and Z-axis directions of a Cartesian coordinate system. That is, if the magnetic field generated by the main magnet (not shown) is directed in the z direction and is termed BO, and the total magnetic field in the z direction is referred to as $B_z$, then $G_x = \partial B_z/\partial x$, $G_y = \partial B_z/\partial y$ and $G_z = \partial B_z/\partial z$, and the magnetic field at any point (x, y, z) is given by $B(x, y, z) = B_0 + G_x X + G_y Y + G_z Z$.

The gradient magnetic fields are utilized in combination with radio frequency pulses generated by transceiver 122, RF amp 123 and RF coil 138 to encode spatial information into the NMR signals emanating from the region of the patient being studied. Waveforms and control signals provided by the pulse control module 120 are utilized by the transceiver subsystem 122 for RF carrier modulation and mode control. In the transmit mode, the transmitter provides a radio frequency waveform modulated in accordance with the control signals to an RF power amplifier 123 which then energizes RF coil 138 which is situated within main magnet assembly 146. The NMR signals radiated by the excited nuclei in the patient are sensed by the same or a different RF coil than is used for transmitting and amplified by a preamplifier 139. The NMR signals are amplified, demodulated, filtered, and digitized in the receiver section of the transceiver 122. The processed NMR signals are transmitted to the array processor 106 for processing by means of a dedicated, unidirectional link 105.

The PCM 120 and SCM 124 are independent subsystems both of which communicate with main computer 101, peripheral system, such as patient positioning system 152, as well as to one another by means of serial communications link 103. The PCM 120 and SCM 124 are each comprised of a 16-bit microprocessor (such as Intel 80286) for processing commands from the main computer 101. The SCM 124 includes means for acquiring information regarding patient cradle position, and the position of the moveable patient alignment light fan beam (not shown). This information is used by main computer 101 to modify image display and reconstruction parameters. The SCM 124 also initiates functions such as actuation of the patient transport and alignment systems.

A patient located in the bore of the magnet may be monitored by ECG electrodes 133. The ECG signal which the electrodes produce is applied to a physiological acquisition controller 135, which produces a trigger signal to the pulse control module 120. This trigger signal demarks the peak (R) in the QRS waveform and is treated herein as the start of the cardiac cycle. As will be described in more detail below, this ECG trigger signal is employed to synchronize the acquisition of each slice.

The gradient coil assembly 136 and the RF transmit and receiver coils 138 are mounted within the bore of the magnet utilized to produce the polarizing magnetic field. The magnet forms a part of the main magnet assembly which includes the patient alignment system 148. A shim power supply 140 is utilized to energize a shim coil associated with the main magnet and which are used to correct inhomogeneities in the polarizing magnet field. In the case of a superconductive magnet, the main power supply 142 is utilized to bring the polarizing field produced by the magnet to the proper operating strength and is then disconnected. The patient alignment system 148 operates in combination with a patient cradle and transport system 150 and patient positioning system 152. To minimize interference from external sources, these NMR system components are enclosed in an RF-shielded room generally designated 144.

Figure 3:
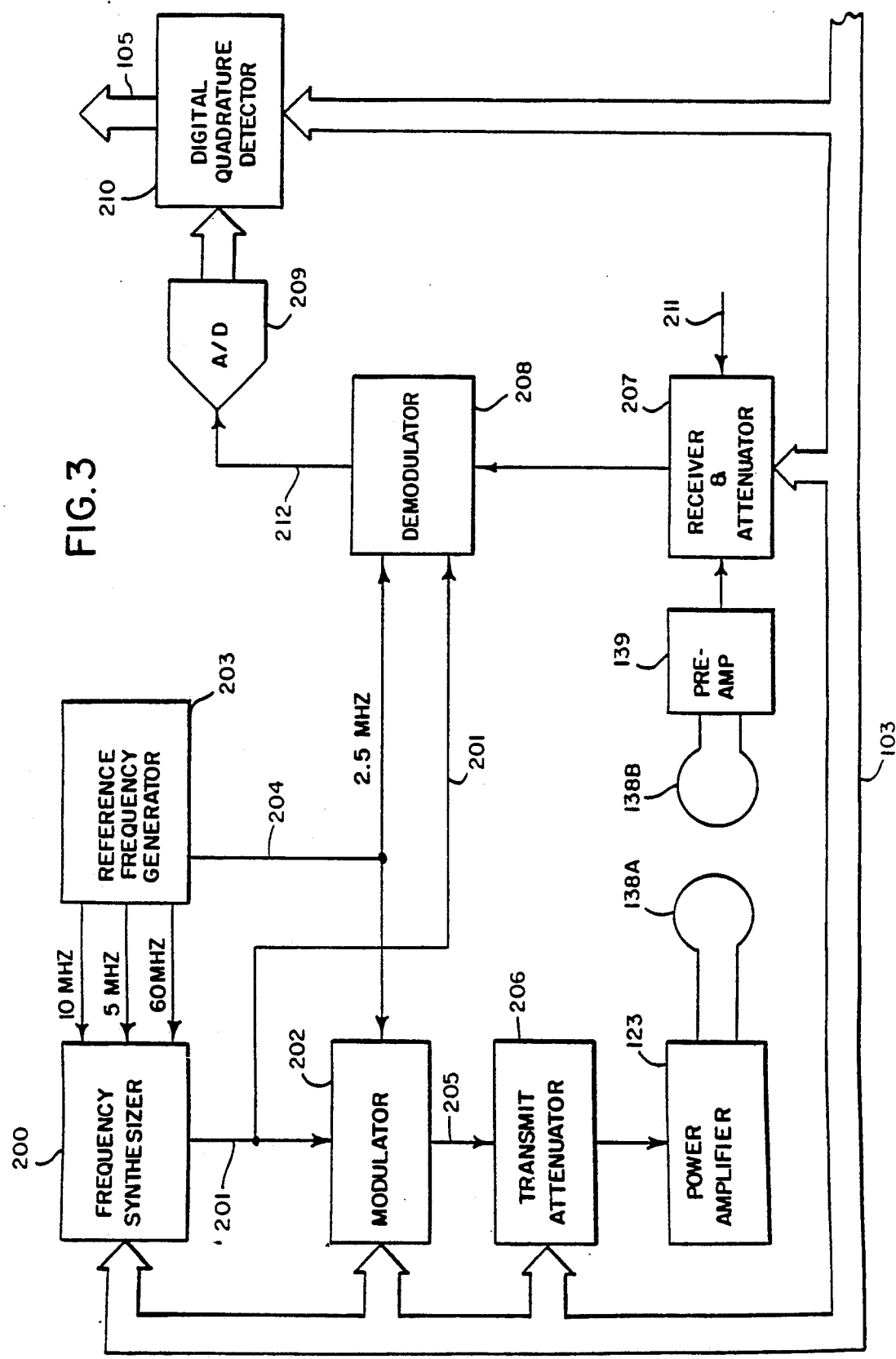
FIG. 3 is an electrical block diagram of the transceiver which forms part of the NMR system of FIG. 1.

Referring particularly to FIGS. 2 and 3, the transceiver 122 includes components which produce the RF excitation field $B_1$ through power amplifier 123 at a coil 138A and components which receive the resulting NMR signal induced in a coil 138B. The base, or carrier, frequency of the RF excitation field is produced under control of a frequency synthesizer 200 which receives a set of digital signals (CF) through the communications link 103 from the main computer 101. These digital signals indicate the frequency and phase of the RF carrier signal which is produced at an output 201. The commanded RF Carrier is applied to a modulator 202 where it is modulated in response to a signal R(t) received through the link 103 from the PCM 120. The signal R(t) defines the envelope, and therefore the bandwidth, of the RF excitation pulse to be produced. It is produced in the PCM 120 by sequentially reading out a series of stored digital values as the RF excitation pulse is produced that represent the desired envelope. These stored digital values may, in turn, be changed by the computer 100 to enable any desired RF pulse envelope to be produced. The magnitude of the RF excitation pulse output through line 205 is attenuated by a transmit attenuator circuit 206 which receives a digital signal, TA, from the main computer 101 through communications link 103. The attenuated RF excitation pulses are applied to the power amplifier 123 that drives the RF transmitter coil 138A. For a more detailed description of this portion of the transceiver 122, reference is made to U.S. Pat. No. 4,952,877 which is incorporated herein by reference.

Referring still to FIGS. 2 and 3, the NMR signal produced by the subject is picked up by the receiver coil 138B and applied to the input of a receiver 207. The receiver 207 amplifies the NMR signal and this is attenuated by an amount determined by a digital attenuation signal (RA) received from the main computer 101 through link 103. The receiver 207 is also turned on and off by a signal through line 211 from the PCM 120 such that the NMR signal is acquired only over the time intervals required by the particular acquisition being performed.

The received NMR signal is at or around the Larmor frequency, which in the preferred embodiment is around 63.86 MHz. This high frequency signal is demodulated in a two step process in a demodulator 208 which first mixes the NMR signal with the carrier signal on line 201 and then mixes the resulting difference signal with the 2.5 MHz reference signal on line 204. The resulting demodulated NMR signal on line 212 has a bandwidth of 125 kHz and it is centered at a frequency of 187.5 kHz. The demodulated NMR signal is applied to the input of an analog-to-digital (A/D) converter 209 which samples and digitizes the analog signal at a rate of 250 kHz. The output of the A/D converter 209 is applied to a digital quadrature detector 210 which produces 16-bit in-phase (I) values and 16-bit quadrature (Q) values corresponding to the received digital signal. The resulting stream of digitized I and Q values of the received NMR signal is output through bus 105 to the array processor 106 where they are employed to reconstruct an image.

To preserve the phase information contained in the received NMR signal, both the modulator 202 in the transmitter section and the demodulator 208 in the receiver section are operated with common signals. More particularly, the carrier signal at the output 201 of the frequency synthesizer 200 and the 2.5 MHz reference signal at the output 204 of the reference frequency generator 203 are employed in both the modulation and the demodulation process. Phase consistency is thus maintained and phase changes in the demodulated received NMR signal accurately indicate phase changes produced by the excited spins. The 2.5 MHz reference signal as well as 5, 10 and 60 MHz reference signals are produced by the reference frequency generator 203 from a common 10 MHz clock signal, and the latter three reference signals are employed by the frequency synthesizer 200 to produce the carrier signal on output 201. For a more detailed description of the receiver, reference is made to U.S. Pat. No. 4,992,736 which is incorporated herein by reference. To improve the SNR of the image, the phased array receiver described in U.S. Pat. No. 5,086,275 and entitled "Time Domain Filtering For NMR Phased Array Imaging," may also be employed.

Figure 4:
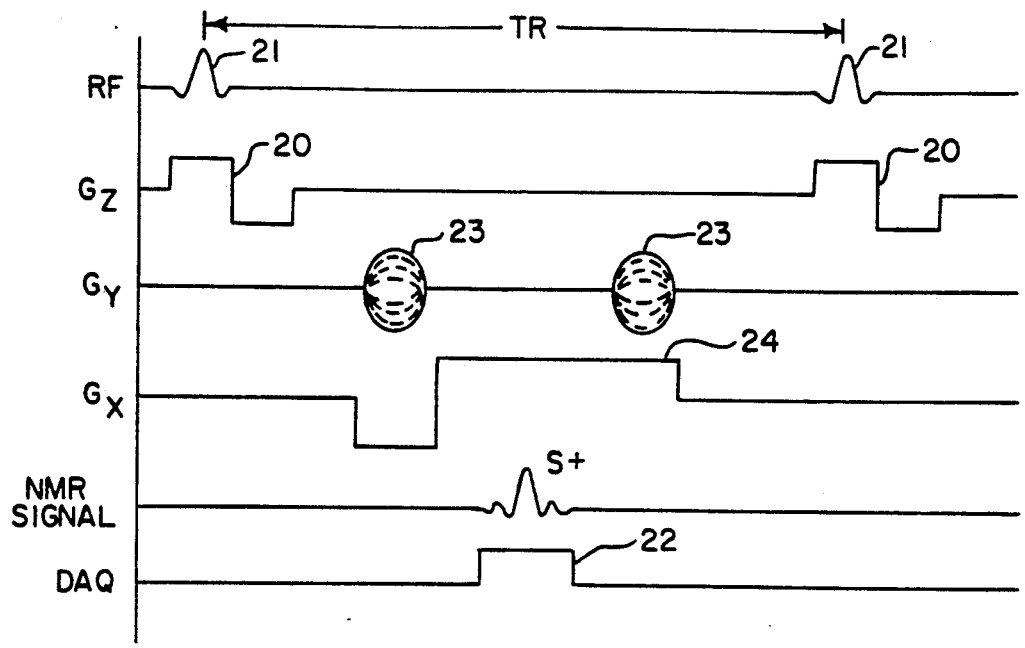
FIG. 4 is a graphic representation of a fast pulse sequence which may be employed by the NMR system of FIG. 2 to practice the present invention.

Referring particularly to FIG. 4, the fast pulse sequence employed in the preferred embodiment of the invention acquires the S+ NMR signal and is known in the art as a gradient refocused acquired steady-state (GRASS) sequence. Ten to fourteen separate slices are typically acquired through a patient's left or right lung, with the $G_z$ slice select gradient 20 being controlled to produce 8 millimeter thick slices with 3 millimeter overlap between slices. The precise number of slices to fully cover a lung depends on the size of the patient. The selective RF excitation pulses 21 provide a flip angle of 20°-25°, which have been determined to provide an optimal signal-to-noise ratio. A short TE of 2.2 msec. at a receiver bandwidth of ±32 kHz is used, and flow-induced dephasing effects are adequately reduced without the use of flow compensation. To reduce the TR to 6.8 msec a partial-echo acquisition of 160 frequency encoded data samples are acquired during a data acquisition window 22 and a $G_x$ readout gradient 24 provides a field of view of 24 centimeters. An effective resolution in the frequency encoding direction (x-axis) of 256 is achieved by employing a homodyne image reconstruction as described in co-pending U.S. patent application Ser. No. 693,895, filed on May 1, 1991 and entitled "High Resolution Imaging Using Short TE and TR Pulse Sequences With Asymmetric NMR Echo Acquisition." The same pulse sequence can be employed when the present invention is applied to the image of peripheral vasculature. In such case, between 30 and 60 separate slices are typically acquired, depending on the patient's size. In the peripheral vessels where the magnetic susceptibility is not as great as in the lungs, flow compensation is usually employed.

During the acquisition of each slice, the GY phase encoding gradient pulses 23 are stepped through 128 discrete values to acquire a corresponding number of "views." As a result, a complete slice can be acquired in less than one second (871 msec.). The order in which these views are acquired is an important teaching of the present invention and will be described in more detail below.

Figure 1:
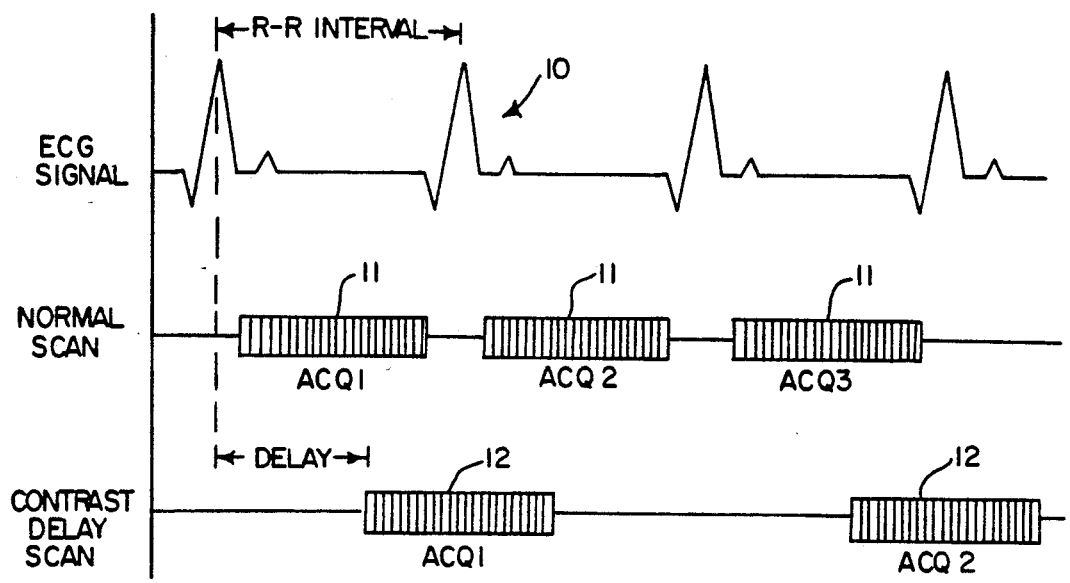
FIG. 1 is a graphic representation of a prior art scan.
Figure 5:
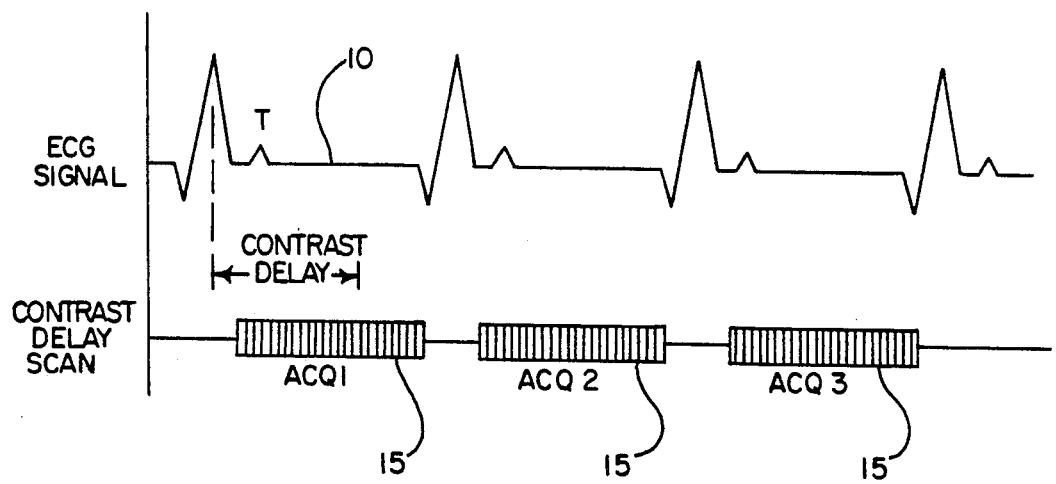
FIG. 5 is a graphic representation of a scan which employs the present invention.

Referring particularly to FIG. 5, a scan according to the present invention is conducted in synchronism with the subject's cardiac cycle. More specifically, after the receipt of the cardiac trigger signal on each R peak of the ECG signal 10, the pulse sequence of FIG. 4 is executed 128 times in succession to acquire an entire 2DFT image data set for one slice through the patient's lung. Regardless of the desired contrast delay, the acquisition is started and completed within the same R-R interval such that a complete slice can be acquired during each successive cardiac cycle as indicated at 15. The desired contrast delay is achieved by altering the order of the 128 views such that the central views are acquired at the desired time delay after the receipt of the cardiac trigger signal. If the same contrast delay is desired in each slice of the scan, then the view order during each successive slice acquisition 15 will be the same. On the other hand, it is also possible to change the contrast delay during successive slice acquisitions to show the vasculature at successive stages of the cardiac cycle. In such a scan, each slice acquisition 15 has a different view ordering in order to provide the desired contrast delays.

Figure 6:
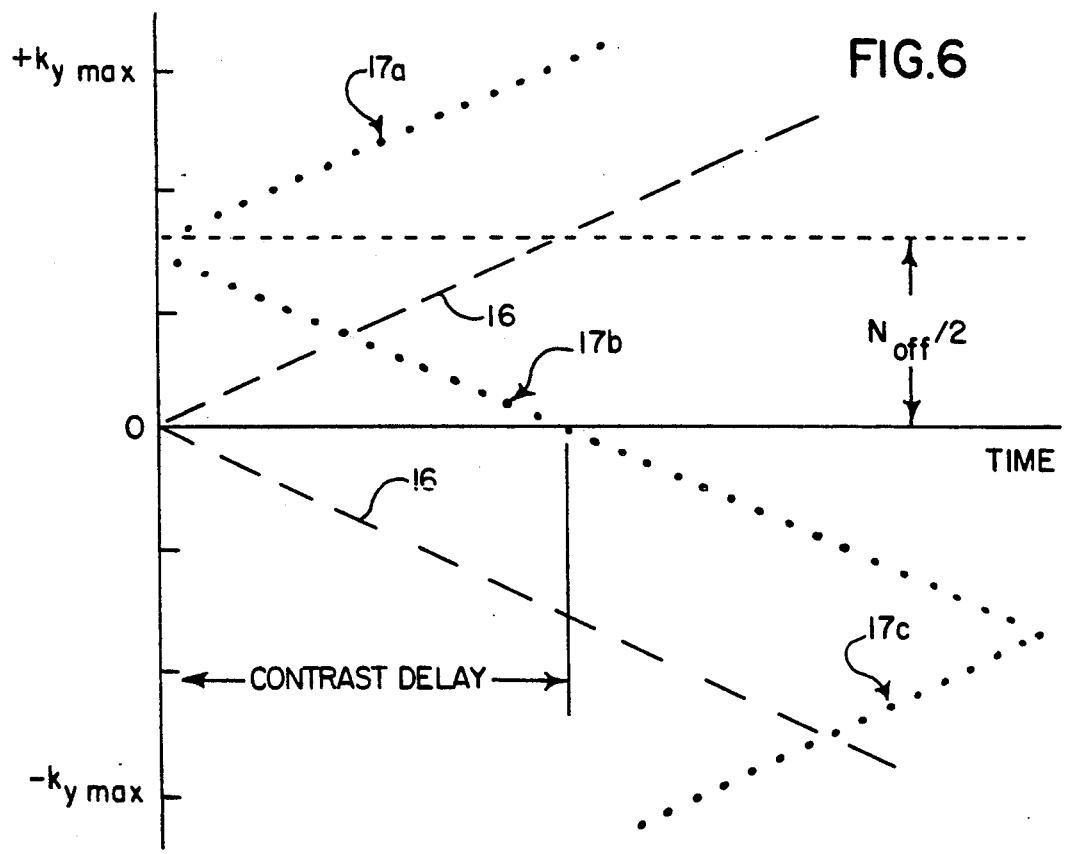
FIG. 6 is a graphic representation of the preferred view ordering which is employed in the scan of FIG. 5.

Referring particularly to FIG. 6, the preferred method for providing the desired contrast delay is to rotate a centric view order by an amount which causes the central, or low order, views to be acquired at the desired time interval after commencement of the acquisition. A conventional centric view order is illustrated by the dashed lines 16 which show the low order views being acquired at the outset of the slice acquisition and progressing outward to the peripheral views steadily during the acquisition ($k_y$=0, +1, -1, +2, -2 . . . +64, -64). Since the image contrast is dominated by the low order views, this conventional centric view order provides virtually no contrast delay effect. On the other hand, if this view order is rotated by an amount $N_{off}/2$ as illustrated by the dotted lines 17, the low order views will be acquired at an interval $N_{off} \times TR$ after the start of the slice acquisition. The resulting image will have an effective contrast delay of this amount because the low order views are the predominant determinant of image contrast. For example, if a contrast delay of 400 msec. is desired:

$N_{off} \times TR = 400$ msec.
$N_{off} = 400/6.8 \approx 59$
$N_{off}/2 \approx 30$.

Consequently, the rotated centric view order would begin at around $k_y = 30$ and successively alternate above and below that value as shown in FIG. 6 by the dotted line 17 (i.e. +31, +29, +32, +28, +33, +27 . . .). When the upper limit ($k_y = +128$) is reached at the right-hand end of line segment 17a, the sequence continues by alternating between values along line segment 17b and the left-hand end of line segment 17c. All 128 views in $k_y$ space are thus sampled.

While the rotated centric view order is preferred because it produces the fewest image artifacts due to the rapid switching of the phase encoding gradient field $G_y$, other view orders are possible. For example, the views can be sampled alternately in plus and minus $k_y$ space and converge at the low order views at the proper time. In the above example of 400 milliseconds, such a sequence might be $k_y = +30, -30, +29, -29$, etc. Other sequences are possible, but the basic requirement is that the low order views which determine the contrast of the image be acquired during the slice acquisition at the desired contrast delay and that the altered view order cause minimal image artifacts.

I claim:

1. An NMR system for conducting a scan in which a set of slice acquisitions are performed to acquire NMR signals which enable a corresponding set of images of a subject to be reconstructed, the combination comprising:

means for generating a polarizing magnetic field;

excitation means for generating an RF excitation magnetic field which produces transverse magnetization in spins subjected to the polarizing magnetic field;

receiver means for sensing an NMR signal produced by the transverse magnetization and producing digitized samples of the NMR signal;

first gradient means for generating a first magnetic field gradient to phase encode the NMR signal;

second gradient means for generating a second magnetic field gradient to frequency encode the NMR signal;

cardiac signal means for generating a trigger signal in synchronism with the subject's cardiac cycle;

pulse control means coupled to the excitation means, first gradient means, second gradient means, cardiac signal means, and receiver means, said pulse control means being operable to conduct the set of slice acquisitions, each slice acquisition comprised of a series of fast pulse sequences which are performed within a single cardiac cycle when a trigger signal is generated, and in which the first gradient means is stepped through a set of phase encoding values ranging from low order values which produce relatively small first magnetic field gradients to high order values which produce relatively large first magnetic field gradients, and in which the order the first gradient means is stepped through its set of phase encoding values by the pulse control means is selected such that the low order values are performed at a preselected contrast delay interval after the generation of the trigger signal.

2. The NMR system as recited in claim 1 in which the first gradient means is stepped in a centric view order, and the centric view order is rotated by an amount which causes the low order values to be performed at said preselected contrast delay interval.

3. The NMR system as recited in claim 1 in which each fast pulse sequence is an SSFP fast pulse sequence.

4. The NMR system as recited in claim 1 in which the preselected contrast delay interval is the same for each slice acquisition in said scan.

5. The NMR system as recited in claim 1 in which the preselected contrast delay interval is different for each slice acquisition in the scan.

6. A method for acquiring NMR data for a complete image of a patient between heart beats and with a preselected image contrast delay, the steps comprising:

producing a cardiac signal which indicates the patient's heart beat;

executing a set of NMR pulse sequences between the heart beats indicated by the cardiac signal to acquire a corresponding set of NMR signals; and reconstructing an image from said set of acquired NMR signals;

wherein each NMR pulse sequence includes the application of a gradient pulse which phase encodes its corresponding NMR signal and the gradient pulse is stepped through a set of values in successive NMR pulse sequences in said set of NMR pulse sequences ranging from low order values which produce relatively small magnetic field gradients to high order values which produce relatively large magnetic field gradients; and wherein the NMR pulse sequences are arranged in an order according to their phase encoding gradient pulse values such that the low order NMR pulse sequences are executed at said preselected image contrast delay after the patient's heart beat.

* * * * *